(12) United States Patent
Freisleben et al.

(10) Patent No.: US 6,316,260 B1
(45) Date of Patent: Nov. 13, 2001

(54) TETRAETHER LIPID DERIVATIVES AND LIPOSOMES AND LIPID AGGLOMERATES CONTAINING TETRAETHER LIPID DERIVATIVES, AND USE THEREOF

(75) Inventors: H.-J. Freisleben, Erzhausen; Emmanouil Antonopoulos, Neu-Isenburg, both of (DE); Maxim Balakirev; Larissa Balakirev, both of Novosibirsk (RU); Klaus Hartmann, Heidelberg; Felix Gropp, Bad Soden, both of (DE)

(73) Assignee: Bernina Biosystems GmbH, Martinsried (DE)

( * ) Notice: Subject to any disclaimer, the term of this patent is extended or adjusted under 35 U.S.C. 154(b) by 0 days.

(21) Appl. No.: 09/294,035

(22) Filed: Apr. 19, 1999

Related U.S. Application Data

(63) Continuation of application No. PCT/EP98/05264, filed on Aug. 19, 1998.

(51) Int. Cl.[7] .......................... C12N 15/63; C12N 15/00; A61K 9/127
(52) U.S. Cl. ................. 435/455; 424/450; 435/320.1; 435/69.1
(58) Field of Search ..................... 435/455, 458, 435/320.1, 69.1; 424/450; 514/44

(56) References Cited

PUBLICATIONS

Anderson (Nature, vol. 392, 25–30), 1998.*
Verma et al. (Nature, vol. 389, pp. 239–242), 1997.*
Christiansen et al., 1975, Int. J. Sys. Bacter. 26:99–101.
Felgner et al., 1987, Proc. Natl. Acad. Sci. 84:7413–7417.
Freisleben et al., 1993, Appl. Microbiol. Biotechnol. 40:745–752.
Gershon et al., 1993, Biochemistry 32:7143–7151.
Langworthy and Pond, 1986, System Appl. Microbiol. 7:253–257.

* cited by examiner

Primary Examiner—Dave Trong Nguyen
(74) Attorney, Agent, or Firm—Akin, Gump, Strauss, Hauer & Feld, L.L.P.

(57) ABSTRACT

Conventional liposomes which are used for transporting pharmaceutical active agents in eukaryotic cells or for lipofection can only be preserved for a limited period, are not acid-stable and require a number of set parameters in order to achieve satisfactory results. Less sensitive liposomes are therefore highly desirable. The inventive tetraetherlipid derivatives are very stable and are well suited to lipofection.

35 Claims, 9 Drawing Sheets

(A)

(B)

(REACTION NO. 1)

(REACTION NO. 2)

(REACTION NO. 3)

(REACTION NO. 4A)

(REACTION NO. 4B)

(REACTION NO. 5)

TETRAETHER LIPID DERIVATIVES AND LIPOSOMES AND LIPID AGGLOMERATES CONTAINING TETRAETHER LIPID DERIVATIVES, AND USE THEREOF

CROSS-REFERENCE TO RELATED APPLICATION

This application is a continuation of International Application PCT/EP98/05264, filed Aug. 19, 1998, the disclosure of which is incorporated herein by reference.

BACKGROUND OF THE INVENTION

The present invention relates to tetraether lipid derivatives, to liposomes and lipid agglomerates containing the inventive tetraether lipid derivatives, and to the use thereof.

Scientific research work requires a great number of methods for the transfection of cells in cell culture and multicellular organisms with nucleic acids. Conventional methods, such as electroporation, DEAE and "calcium phosphate"-supported transfection, microinjection or ballistic methods, have the drawback that the transfection efficiencies achieved by them are often poor, that the cell survival rates are very small and/or that they cannot be performed on multicellular organisms. Although viral and retroviral transfection systems are more efficient, they have risks of their own, such as an increased immune response or an uncontrolled integration into the target genome. Therefore, transfection of nonviral nucleic acids with the aid of liposomes, also called lipofection, is a successful and frequently employed alternative to the above-described methods.

Liposomes are artificially produced unilamellar or multilamellar lipid vesicles which enclose an aqueous interior. They are in general similar to biological membranes and, therefore, they are often easily integrated into the membrane structure after attachment to the membranes. During this membrane fusion the contents of the liposome interior is discharged into the lumen which is enclosed by the biological membrane. Alternatively, the liposomes are moved by endocytotic processes into the cytosol of the cell to be transfected; subsequently they are either destroyed in the cytosol or they interact as such with the nuclear membrane. In the last-mentioned case the compounds contained in the aqueous interior of the liposome are substantially protected against proteolytic or nucleolytic attacks.

Therefore, liposomes can be used as transport vehicles for substances, such as nucleic acids or pharmaceuticals. For instance, the cosmetic industry produces liposome-containing creams for skin care which transport active agents in a target-directed manner into the epidermis or lower cell layers. Natural lecithins of soybean or egg yolk and defined natural or artificial phospholipids, such as cardiolipin, sphingomyelin, lysolecithin, and others, are mainly used for the preparation of liposomes. Size, stability and absorbency as well as the release of the associated molecules are influenced by varying the polar head groups (choline, ethanolamine, serine, glycerine, inosite), the length as well as the saturation degrees of the hycrocarbon atom chains.

One of the essential drawbacks of the liposomes thus far known is their low stability. Even in a cooled state liposomes which are formed from normal bilayer-forming phospholipids are only durable for a short period of time. Although their storage stability can be increased e.g. by the inclusion of phosphatidic acid, the stability improved thereby is still inadequate for many purposes. Moreover, conventional liposomes are not acid-stable and are thus neither suited for the transport of pharmaceutical active agents which pass through the stomach after oral administration, nor for the liposome-supported DNA transfection under slightly acid pH conditions.

Liposome-forming lipid mixtures, such as Lipofectamin®, Lipofectin® or DOTAP®, are often used in mammalian cells for scientific or medicinal lipofections. Apart from the already mentioned drawbacks, their use requires an exact determination of a multitude of parameters (such as cell density, amount of nucleic acid, amount of the lipids, volume of the liposome batch, etc.) because there is only a very limited range of optimum parameters within which an adequate transfection efficiency can be achieved. As a result, transfections using commercial lipofection reagents become very troublesome and expensive. Furthermore, great variations between the individual charges can be observed in the above-mentioned products, which makes them hardly reliable in practice.

SUMMARY OF THE INVENTION

Therefore, it is the object of the present invention to prepare lipofection agents which exhibit an enhanced mechanical and chemical stability and thus a prolonged storage stability and which permit a simple and reliable use.

According to the invention this object is achieved by providing tetraether lipid derivatives (also abbreviated hereinafter as "TEL derivatives") represented by the general formula (I):

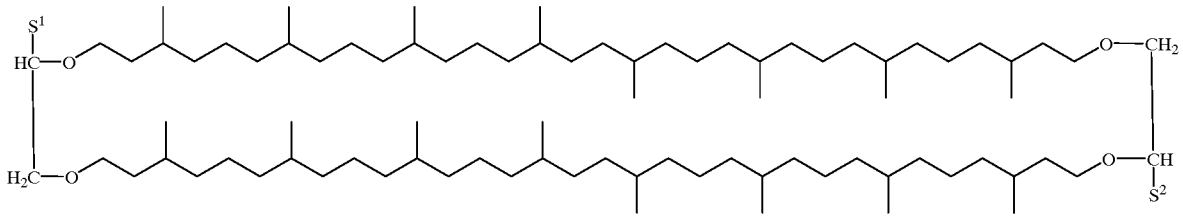

wherein $S^1$ and $S^2$ may be the same or different and respectively have the following meaning:

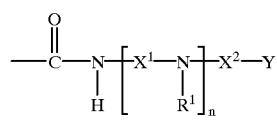

and

Y may be $-NR^2R^3$ or $-N^{\oplus}R^4R^5R^6$;

$X^1$ and $X^2$ may be the same or different and are respectively selected independently of each other from the group comprising a branched or unbranched alkylene or alkenylene having 2 to 20 carbon atoms;

$R^1$ to $R^6$ may be the same or different and are respectively selected independently of each other from the group comprising hydrogen, branched or unbranched alkyl, alkenyl, aralkyl or aryl groups having 1 to 12 carbon atoms, wherein a respective one of the moieties $R^2$ to $R^6$ may further comprise an antibody against cell surface molecules or a ligand for cell surface receptors; and n may be an integer between 0 and 10, and modifications thereof formed by the formation of pentacycles in the basic tetraether skeleton.

The lipid skeleton of the tetraether lipid derivatives according to the invention consists of a 72-membered macrotetraether cycle, the basic skeleton of which is a dibiphytanyl-diethyl-tetraether heterocycle. In this skeleton the ω-carbon atoms of the phytanyl chains of two respective diether molecules are covalently linked to each other. Tetraether lipids are already known and have so far exclusively been detected in archaebacteria. In response, for instance, to the cultivation temperature, pentacycles can be formed within the dibiphytanyl chains, the pentacycles giving the lipid a specific physicochemical character. With each pentacyclization the basic skeleton loses two hydrogen atoms. A summary of all of the basic structures of archaebacterial lipids so far known can be found in Langworthy and Pond (System Appl. Microbiol. 7, 253–257, 1986).

According to the invention the naturally occurring lipid skeleton has now been derivatized to be suited for incorporation into liposomes or lipid agglomerates provided for transfection. To this end side chains are introduced that are positively charged either per se through the formation of quatemary ammonium salts or under physiological conditions, i.e. at a pH of 7.35 to 7.45. Lipids derivatized in this manner are particularly well suited for contacting negatively charged molecules, e.g. nucleic acid molecules, and for enclosing the same, for instance in liposomes. Since a possible intended use of the lipids according to the invention may be the formation of liposomes or lipid agglomerates for genetic therapeutic applications, the lipids according to the invention can additionally be coupled with molecules that enable the lipids to specifically dock onto special cells. Examples thereof are antibodies against cell surface antigens, in particular those that are selectively expressed on the target cells. Suited are also ligands for receptors which are selectively found on the surface of specific cells, as well as biologically active peptides which permit an organ- or cell-specific targeting in vivo (Ruoslati, Science, 1997). The latter have also been designated as ligands for the purposes of the present application.

The special advantage of the tetraether lipid derivatives according to the invention is that their lipid skeleton is devoid of any double bonds and therefore insensitive to oxidation. Furthermore, instead of the lipid ester bonds contained in lipids consisting of eubacteria and eukaryotes, it only contains lipid ether bonds which are not attacked—even at high proton concentrations as are e.g. found in the stomach.

In preferred embodiments the substituents $S^1$ and $S^2$ are the same at both ends of the basic tetraether lipid skeleton. Starting from natural tetraether lipids, this permits a synthesis without the intermediate use of protective groups. An identity of the substituents $S^1$ and $S^2$ is particularly preferred in such cases where none of the moieties $R^1$ to $R^6$ represents an antibody or ligand for a cell surface receptor.

In a preferred embodiment of the tetraether lipid derivative according to the invention, group $X^1$, both in $S^1$ and $S^2$, represents an alkylene or alkenylene having 2 to 10, preferably 3 to 6 carbon atoms. In quite particularly preferred embodiments $X^1$ is propylene.

Group $X^2$ is also preferably an alkylene or alkenylene having 2 to 10, preferably 3 to 6 carbon atoms. Propylene residues are also particularly preferred for $X^2$.

n may be 0 to 10. In preferred embodiments n may be 0 to 3, 0 being quite particularly preferred.

The tetraether lipid derivatives according to the invention are preferably prepared from natural tetraether lipids which can e.g. be isolated from archaebacteria. As has already been mentioned above, pentacycles are found to a certain extent within the dibiphytanyl chains in the tetraether lipids isolated from natural sources. The extent of pentacyclization can be influenced by the cultivation temperature. Normally, 0 to 8 pentacycles are found per basic tetraether skeleton, with most of the lipid molecules having between 1 and 5 pentacycles at a cultivation temperature of 39°, whereas predominantly 3 to 6 pentacycles are observed at a cultivation temperature of 59°. The following table furnishes information about the pentacyclization distribution at a cultivation temperature of 39° C. and 59° C., respectively:

TABLE

| Number of pentacycles | Percentage at a cultivation temperature of 39° | Percentage at a cultivation temperature of 59° C. |
| --- | --- | --- |
| 0 | 5.5 ± 0.5 | 6.6 ± 0.5 |
| 1 | 17.3 ± 0.4 | 9.2 ± 1.2 |
| 2 | 23.0 ± 4.0 | 9.4 ± 0.05 |
| 3 | 23.4 ± 0.5 | 17.1 ± 1.4 |
| 4 | 14.8 ± 1.3 | 19.0 ± 1.3 |
| 5 | 10.8 ± 1.0 | 21.6 ± 0.3 |
| 6 | 3.6 ± 0.0 | 11.7 ± 0.2 |
| 7 | 1.2 ± 0.5 | 4.7 ± 0.3 |
| 8 | 0.5 ± 0.4 | 0.8 ± 0.3 |

In further embodiments of the tetraether lipid derivatives according to the invention Y stands for —$NR^2R^3$ in both $S^1$ and $S^2$ $R^2$ and $R^3$ are preferably hydrogen, branched or unbranched alkyl, alkenyl, aralkyl or aryl groups, particularly preferably hydrogen, methyl, ethyl or propyl groups. In a further preferred embodiment Y in both $S^1$ and $S^2$ represents a quaternary ammonium salt, the moieties $R^4$, $R^5$ and $R^6$ of which are also preferably hydrogen, branched or unbranched alkyl, alkenyl, aralkyl or aryl groups having 1 to 12 carbon atoms, particularly preferably hydrogen, methyl, ethyl or propyl. One of the moieties $R^2$ to $R^6$ may respectively comprise an antibody against cell surface molecules or a ligand for cell surface receptors.

In particularly preferred embodiments the tetraether lipid derivative according to the invention has the general formula (I) with the following substituents $S^1$ and $S^2$:

Compound A:

$S^1$ and $S^2$: —CO—NH—$(CH_2)_3$—$NH_2$;

Compound B:

$S^1$ and $S^2$: —CO—NH—$(CH_2)_3$—$N(CH_3)_2$:

Compound C:

$S^1$ and $S^2$: —CO—NH—$(CH_2)_3$—$N^{\oplus}(CH_3)_3$.

The inventive tetraether lipid derivatives can e.g. be isolated from the total lipid extract of archaebacteria, e.g. from the total lipid extract of the archaebacterium *Thermoplasma acidophilum*. Thermoplasmas grow between pH 1 and 4 and at temperatures of 33° C. to 67° C. *Thermoplasma acidophilum* can be cultivated, as indicated in Example 1.

Normally, a culture of the microrganism which has been cultivated up to an $OD_{578}$ of about 0.6 is harvested, and the harvested microorganisms are either directly used for lipid isolation or are freeze-dried and stored. For the isolation of the tetraether lipids from the total lipid extract of *Thermoplasma acidophilum* the extract is subjected to acid hydrolysis to produce tetraether (Example 2 and FIG. 7). Oxidation of the free hydroxyl groups on the tetraether into dicarboxylic acid compounds, reaction of said dicarboxylic acid compounds with $SOCl_2$, and reaction of the resulting carboxylic acid chlorides with amines results in the formation of different tetraether lipid derivatives (Example 3 and FIG. 7).

The TEL derivatives according to the invention can be used for preparing lipofection agents. Lipofecton agents are e.g. liposomes or lipid agglomerates. Methods for preparing liposomes are generally known. In general, the lipid provided for the preparation of the liposomes is first dissolved in an organic solvent and a lipid film is formed by evaporation. The lipid film is thoroughly dried to remove all of the solvent residues. Subsequently, the lipids of said film are resuspended in a suitable buffer system. For medicopharmaceutical purposes physiological saline, pH 7.4, is e.g. suited, but other buffer systems (e.g. McIlvaine buffer) or unbuffered solutions, such as unbuffered potassium or sodium chloride solutions, can also be used. The buffer amount should be calculated such that it later yields a liposome dispersion with not more than 15–20 mg lipid/ml buffer. Large multilamellar vesicles having a size distribution within the μm range can first be formed by manual shaking. The formation of such vesicles can be facilitated by using two small glass beads and/or an ultrasonic bath of low sound intensity. The following methods were tested for the actual preparation of unilamellar liposomes of a defined size and were considered to be suited for the preparation of liposomes from tetraether lipid derivatives according to the invention:

(a) Ultrasonic treatment: The suspension of multilamellar liposomes is sonicated at 20 kHz for 5 minutes (Branson Sonifer B 15). Liposomes having a diameter of about 500 nm are formed.

(b) Extrusion by means of a French press cell: The suspension of multilamellar liposomes is extruded in the French press cell at 16,000 p.s.i. four times (SLM-Aminco Inc., Urbana Ill., USA). Liposomes having a diameter of about 120 nm are formed.

(c) Extrusion by polycarbonate filter: The suspension of multilamellar liposomes is extruded by polycarbonate filters of a defined pore size (LiposoFastn'", Avestin, Ottawa, Canada). The use of filters having a pore size of 100 or 200 nm will yield liposomes which, as far as size distribution is concerned, are slightly above the pore size. The extrusion by filters of such a small pore size can simultaneously serve as sterile filtration provided that all of the other preconditions for a sterile filtration (e.g. exact separation of the unsterile and sterile sides of the filtration apparatus) are observed. To facilitate the filtration process, a few preparatory measures can be taken:

(ca) The suspension of multilamellar liposomes is sonicated at 20 kHz between 1 and 5 minutes (see (a)).

(cb) The suspension of multilamellar liposomes is frozen 1 to 3 times and rethawed.

(cc) The suspension of multilamellar liposomes according to (ca) or (cb) is prefiltered by a polycarbonate filter having a pore size of 600 to 800 nm.

Subsequent to the ultrasonic treatment or extrusion, the liposomes can be centrifuged in an Eppendorf centrifuge 3200 for 10 minutes to remove non-liposomal material. Intact closed vesicles remain in the supernatant.

Liposomes can further be prepared by detergent solubilization with subsequent detergent dialysis. To this end, a lipid film is first formed, as described above. The lipid film is suspended in a detergent-containing buffer system (examples of dialyzable detergents: octyl-β-D-glucopyranoside or octyl-β-D-thioglucopyranoside). The molar ratio (TEL derivative: detergent) should be between 0.05 and 0.3 in the case of said detergents and the buffer amount should be calculated such that a liposome dispersion of not more than 15–20 mg lipid per ml buffer is obtained at a later time. Mixed micelles of detergent and TEL derivative are formed by manual shaking.

The suspension of mixed micelles is now transferred into dialysis tubes, for example a Lipoprep® dialysis cell or a mini-Lipoprep® dialysis cell (Diachema AG, Langnau, Switzerland), and is dialyzed at room temperature for 24 hours. Upon removal of the detergent by dialysis, liposomes having a diameter of about 400 nm are formed from the mixed micelles.

The liposome preparation can be centrifuged in an Eppendorf centrifuge 3200 for 10 minutes to remove non-liposomal material. Intact closed vesicles remain in the supernatant.

The lipid agglomerates according to the invention consist of one or several layers of the TEL derivatives according to the invention. Negatively charged molecules, e.g. nucleic acid molecules, can be intercalated between two of such layers.

Lipofection agents which consist of TEL derivatives according to the invention of up to 100% have turned out to be extremely stable, storable for an almost indefinite period of time and impenetrable to protons. For many applications, including the formulation of pharmaceuticals comprising acid-labile active agents, and for the transfection of eukaryotic cells, pure TEL-derivative lipofection agents are therefore the means of choice.

The preparation of lipofection agents which, apart from an amount of TEL derivative, contain standard bilayer-forming phospholipids has also turned out to be of advantage, the weight percentage being here based on the total lipid (mixed liposomes or mixed lipid agglomerates). Mixed lipofection agents are prepared by analogy with the preparation of pure TEL derivative lipofection agents.

These bilayer-forming phospholipids may e.g. be sphingomyelins, cephalins, lecithins and cardiolipins. Particularly preferred is the addition of cationic lipids, such as DOTMA (N-[1 -(2,3-dioleyloxy)propyl]-N,N,N-trimethylammoniumchloride) (Life Technologies, Gaithersberg, USA) or DOTAP (N-[1-(2,3-dioleoyloxy)propyl]-N,N,N-trimethylammoniumchloride) (Boehringer Mannheim, FRG) or DOSPER (Boehringer Mannheim). For the promotion of the transfection efficiency neutral lipids such as DOPE (dioleoylphosphatidylethanolamine) (Sigma) can also be used in the preparation of the TEL derivative liposomes (Example 5). In a further preferred embodiment cholesterol and/or its derivatives are incorporated into the membrane. Moreover, any further lipid that is suited for forming liposomes or lipid agglomerates can be used. The particular advantage of the mixed lipofection agent according to the invention is its stability which is improved (enhanced) by the TEL derivative amount, as compared with e.g. liposomes without a TEL derivative amount.

In the mixed lipofection agents according to the invention the ratio of tetraether lipid derivative to further lipids is preferably 5:1 to 1:5. In particularly preferred embodiments the ratio is 1:2 to 1:0.5, particularly preferred is 1:1. All information is based on weight ratios.

The expressions "TEL derivative liposome", "liposome of pure TEL derivative", etc. will refer in the following to liposomes the lipid amount of which consists of up to 100% of TEL derivatives according to the invention, preferably TEL of *Thermoplasma acidophilum*. The same is applicable to the expressions "tetraether lipid derivative agglomerate" and related expressions.

"Mixed liposomes" and "mixed lipid agglomerates" additionally comprise conventional phospholipids, and the expressions "liposome" or "lipid agglomerate" comprise both liposomes and lipid agglomerates of pure TEL derivatives as well as mixed liposomes or mixed lipid agglomerates.

The inventive liposomes, including the mixed liposomes, and the lipid agglomerates, including the mixed agglomerates, can serve as transport vehicles for nucleic acids and/or cosmetic, pharmaceutical active agents. Moreover, the liposomes and lipid agglomerates according to the invention permit a target-directed gene transfer. To this end nucleic acids, such as DNA or RNA sequences, which contain genes or gene fragments and are present in linear form or in the form of circularly closed vectors, which may contain further genetic material, are packed into pure TEL liposomes or mixed liposomes, pure lipid agglomerates and mixed agglomerates and are added to the cells to be transfected in vitro or in vivo. Moreover, when the liposome membrane or agglomerate surface contains antibodies for which corresponding proteins or peptides are present on the cells to be reached by way of gene therapy, a contact between liposome or agglomerate surface and target cell is promoted by the contact between the antigen on the target cell and the antibody in the membrane of the inventive liposome or the agglomerate surface, respectively.

Furthermore, the invention relates to a pharmaceutical composition which contains the liposomes or lipid agglomerates according to the invention.

The liposomes and/or lipid agglomerates according to the invention are preferably used as transport vehicles in those active agents in the case of which an oral application is not possible for the reason that these active agents would be inactivated in the acid gastric juice or would be degraded by lipases or peptidases in the small intestine. However, the liposomes and lipid agglomerates according to the invention are acid-stable and can therefore pass in unhindered form through the stomach, e.g., into the small intestine, and render resorptive enclosed active agents which upon oral application can normally not pass into the blood stream. The active agents may be contained in the aqueous lumen of the liposome, they may be present between the layers of the lipid agglomerates or integrated thereinto. In case the active agent to be transported is a nucleic acid, it is most of the time protected in the liposome or between the agglomerate layers. In a further embodiment the active agent is covalently bound to the TEL which is contained in the liposome. Preferred active agents are e.g. cytostatics, immunosuppressants, immunostimulants or vaccines as well as hormones. The localization of the active agent in the lumen or in the membrane depends on the water or lipid solubility thereof and is determined by the oil/water distribution coefficient. Many active agents have an intermediary distribution, i.e. both a certain water and lipid solubility according to which they are distributed within a liposome over lumen and membrane. Further examples of active agents which are dissolved in the lumen are vaccines, hormones and water-soluble amounts or derivatives of daunorubicin and doxorubicin or methylprednisolone. A preferred methylprednisolone derivative is the sodium salt of the methylprednisolone hydrogen succinate. By contrast, preferably covalently bound active agents are e.g. antibodies, hormones, lectins and interleukins or active fragments of said groups of substances.

It could be shown that the liposomes or lipid agglomerates according to the invention can interact with cell membranes in a particularly satisfactory manner. For instance, the absorption of tetraether lipid derivatives, coupled with the lipophilic fluorescence dye rhodamine, by the cell membrane of Baby Hamster Kidney (BHK) cells could be detected (see FIG. 1 and Example 5.2).

Therefore, tumors could also be fought in a purposeful manner with the liposomes or lipid agglomerates according to the invention by incorporating e.g. tumor-specific antibodies or antibody fragments into the liposome membrane that guide the liposomes of the lipid agglomerates, which are filled with active agents, into tumor cells in a target-directed manner. A chemotherapeutical treatment with target-directed active chemotherapeutics helps to drastically reduce undesired side effects.

In a further embodiment of the invention the TEL derivatives according to the invention, either in pure form or as a component of pure or mixed liposomes or lipid agglomerates, serve as a basis for the preparation of medical ointments or creams for the skin.

A further possible application for the TEL derivative according to the invention, for liposomes or lipid agglomerates of pure TEL derivatives from *Thermoplasma acidophilum* or for the mixed liposomes or mixed lipid agglomerates containing said TEL derivatives is the use of said substances in the field of medical diagnostics. For instance microtiter plates can be coated with TEL derivatives, TEL derivative liposomes or TEL-derivative mixed liposomes which have been obtained by conjugation with specific antibodies or antigens. Carriers coated in this way can e.g. be used for the immunometric determination of proteins, peptides or metabolic products.

The following figures and examples will explain the invention:

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1A is a phase-contrast photograph;

FIG. 1B shows the fluorescence photographed with red-emission and green-extinction filters;

Figure 1:
FIG. 1 shows micrographs of BHK cells which have been preincubated with rhodamine-linked tetraether lipid derivative B (10 $\mu$g/ml) for 70 min.
Figure 1:

lane 1: size marker (λHindIII: 23130, 9416, 6557, 4361, 2322, 2027, 5634 and 125 bp)

lane 2: molar DNA-to-lipid ratio of 1:0 lane 3: molar DNA-to-lipid ratio of 1:0.7 lane 4: molar DNA-to-lipid ratio of 1:1.4 lane 5: molar DNA-to-lipid-ratio of 1:2.1 lane 6: molar DNA-to-lipid ratio of 1:2.8.

Figure 4:
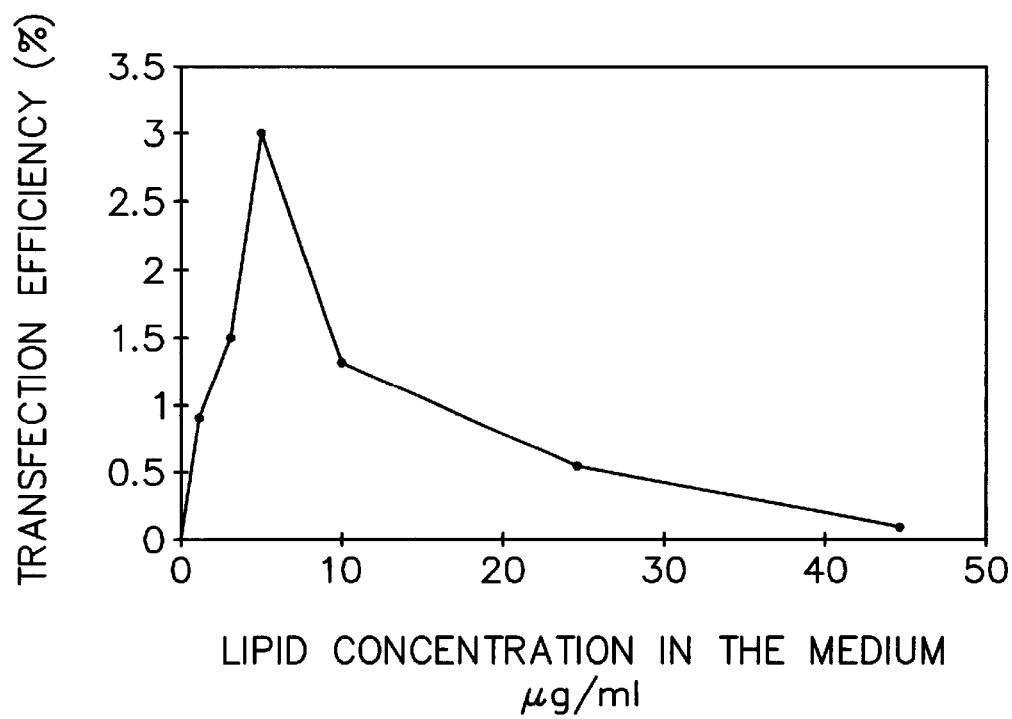

FIG. 4 shows the efficiency of the transfection of BHK cells with the tetraether lipid derivative B at a constant DNA concentration of 1.4 μg/ml in response to the lipid concentration in the medium. Identical results have been obtained with compounds A and C.

Figure 5:
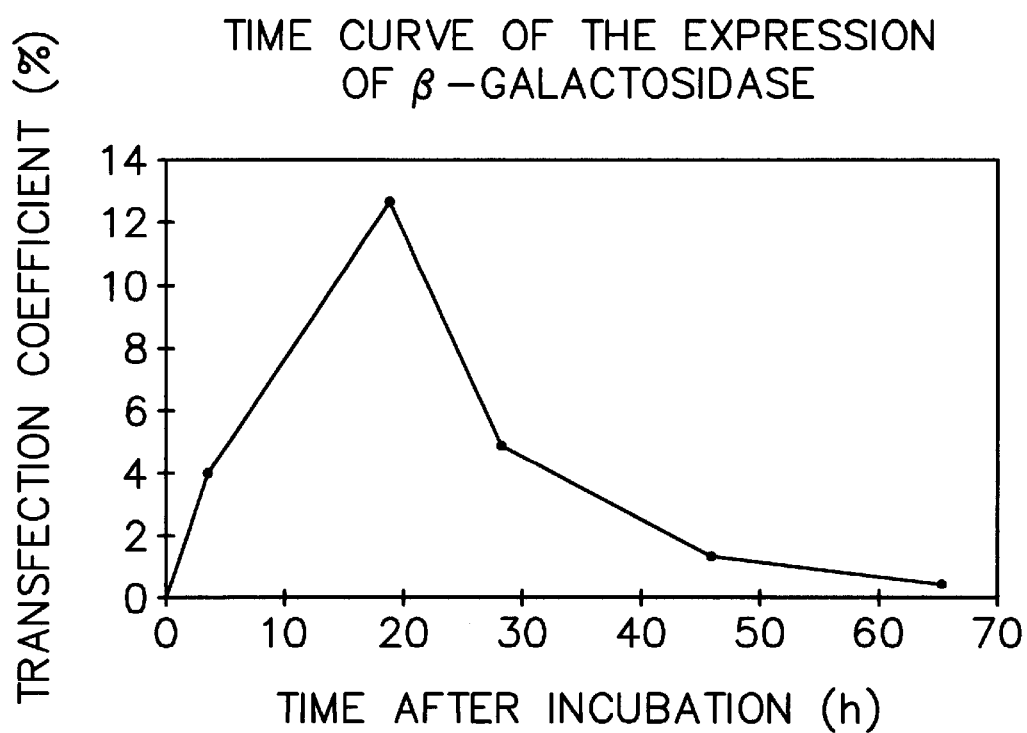

FIG. 5 shows the time curve of the expression of β-galactosidase after incubation of BHK cells with tetraether lipid derivative complexes, which contained the plasmid pSV-lac (Promega) coding for β-galactosidase. 1.2 μg DNA and 5 μg tetraether lipid derivative B were used per transfection batch. Identical results have been obtained with tetraether lipid derivatives A and C.

Figure 6:
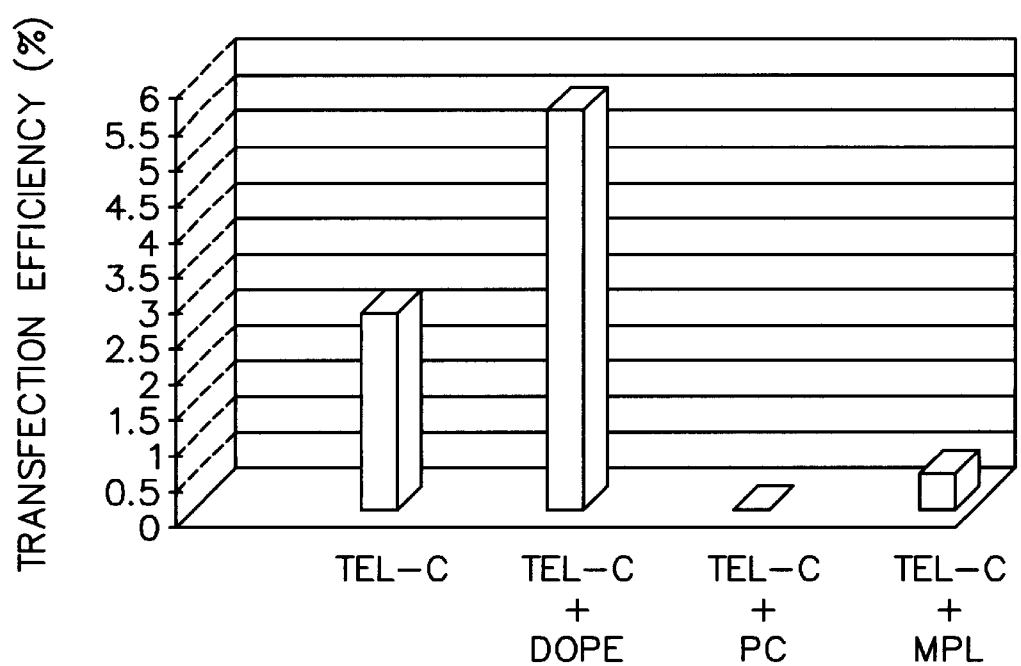

FIG. 6 shows the transfection efficiency of pure tetraether lipid derivative liposomes in comparison with mixed liposomes with DOPE (molar ratio 1:1), PC (molar ratio 1:1) and MPL (molar ratio of tetraether lipid derivative B to MPL as 1:2) (MPL: "main phospholipid" from *Thermoplasma acidophilum*, total phospholipid fraction, see PCT/EP97/0101 1). The results with derivatives A and B are comparable.

FIG. 7 shows the reaction scheme for the synthesis of different TEL derivatives. The tetraether macrocylce is here represented by the central rectangle in each formula. There is shown in detail in FIG. 7a the reaction of a natural tetraether lipid, e.g. isolated from *Thermoplasma acidophilum*, with 1 molar hydrochloric acid in methanol for removing the sugar residues to obtain dihydroxylic compound (2). Compound (2) is then reacted to obtain dicarboxylic acid (3).

Figure 7A:
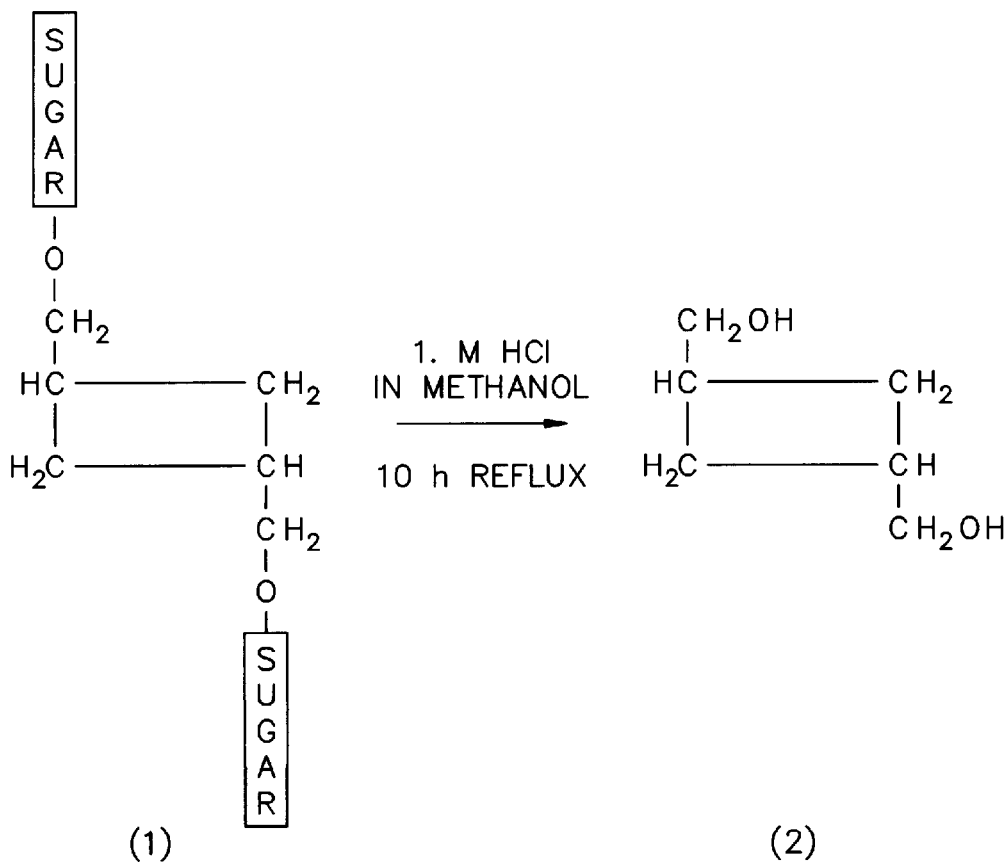
Figure 7A:
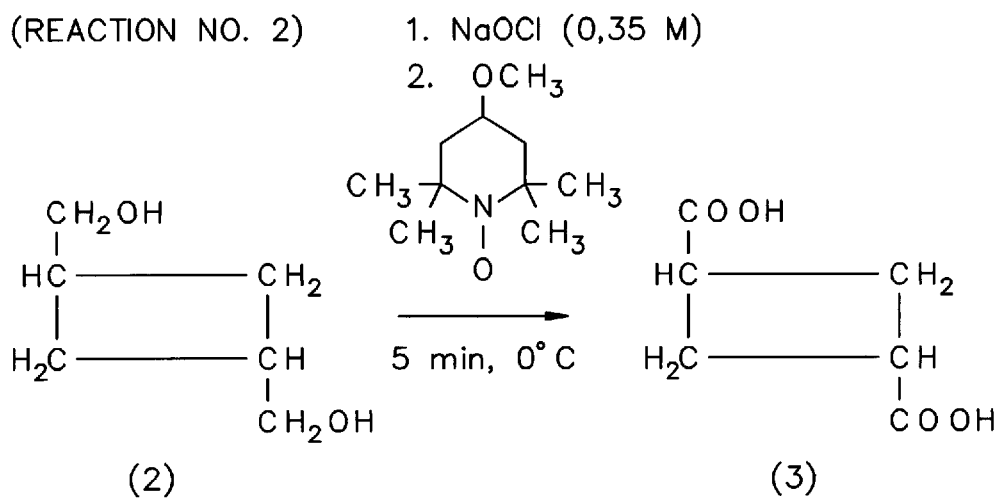
Figure 7B:
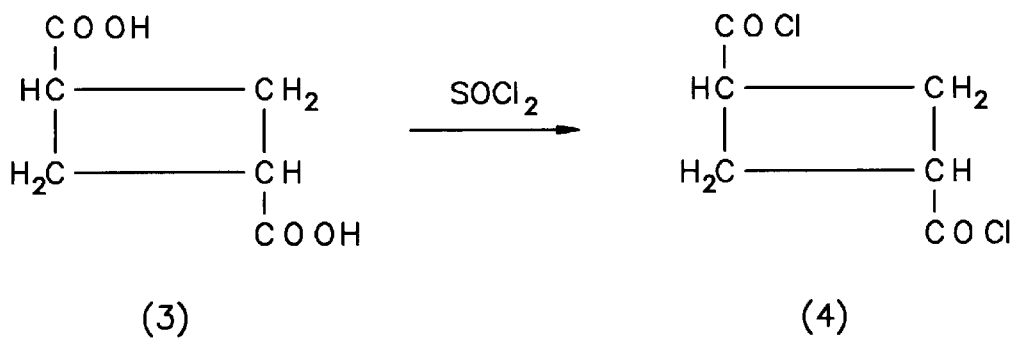
Figure 7B:
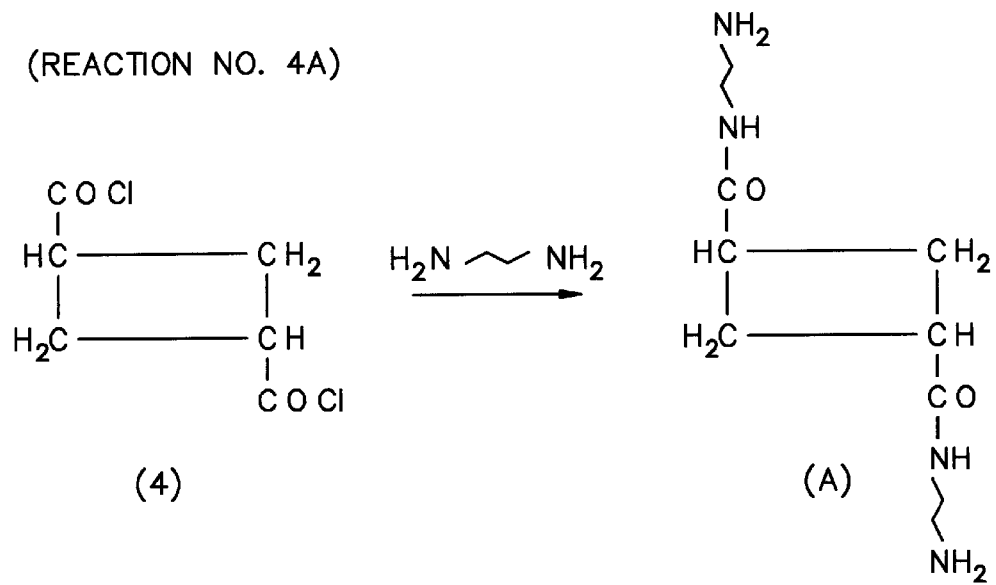

FIG. 7b the reaction of dicarboxylic acid (3) to obtain the corresponding dicarboxylic acid chloride (4). The dicarboxylic acid chloride serves as a starting material for the reaction with amines. According to reaction 4a, 1,3-diaminopropane is reacted to obtain tetraether lipid derivative (A). According to reaction no. 4b, the dicarboxylic acid chloride is reacted with 3-dimethylaminopropylamine to obtain tetraether lipid derivative B.

Figure 7C:
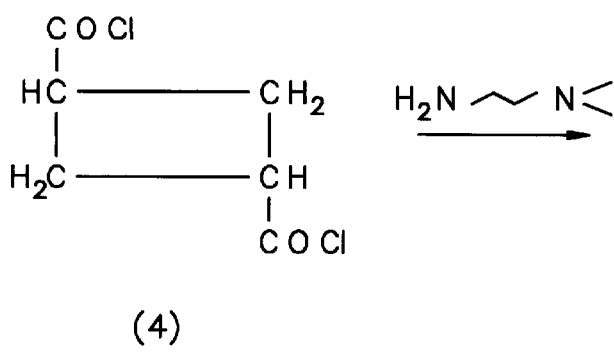
Figure 7C:
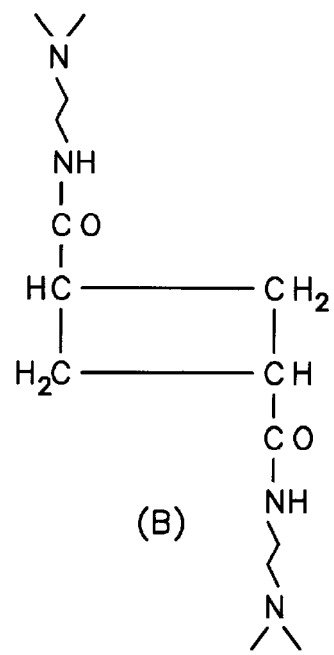
Figure 7C:
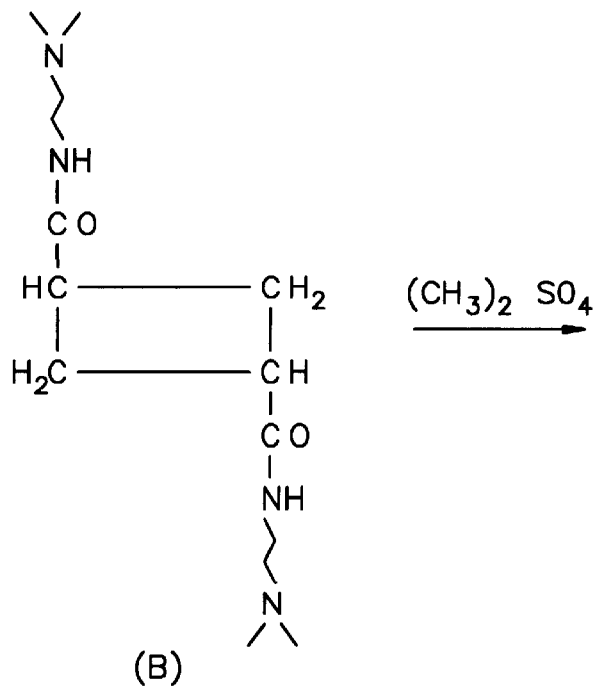
Figure 7C:
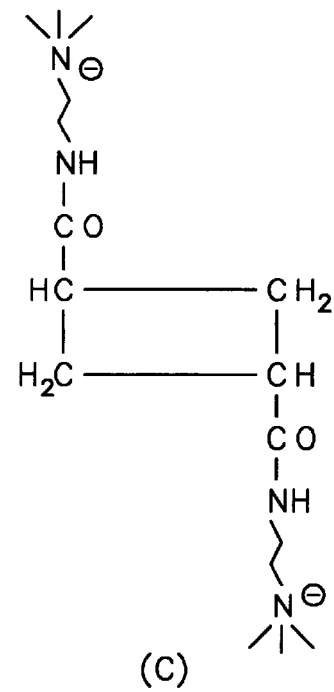

FIG. 7c the tetraether lipid derivative B which reacts with dimethyl sulfate to obtain tetraether lipid derivative C.

DETAILED DESCRIPTION OF THE INVENTION

EXAMPLE 1

Cultivation and Conservation of *Thermoplasma acidophilum*

1.1 Medium

The culture medium for *Thermoplasma acidophilum* consists of Freundt's medium (Christiansen et al., (1975)), a 20% (w/v) glucose solution and a 20% (w/v) yeast extract solution (Difco). The Freundt's medium is sterilized in situ at 120° C., the 10-l fermenter for 25 min and the 50-l fermenter for 45 min. The glucose and yeast solutions are separately sterilized at 110° C. for 10 min and only added to the medium immediately prior to inoculation.

1.1.1 For inoculation with frozen cells 94% by volume of Freundt's medium, 5% by volume of glucose solution and 1% by volume of yeast extract solution are added.

1.1.2 For inoculation with a suspension culture 84% by volume of Freundt's medium, 5% glucose solution and 1% Difco solution are combined as above.

1.2 Inoculation 2.1 In the case of a culture from frozen cells 1 ml/l frozen cells are added to the medium described in 1.1. The lag-phase is 2 to 3 days.

2.2 For cultures with suspension culture inoculum 10% by volume of suspension culture are added to the medium described in 1.2. The lag phase is in this case only a few hours.

1.3 Cultivation of *Thermoplasma Acidophilum*

*Thermoplasma acidophilum* is preferably cultivated in 10-l or 50-l fermenters. All of the fermenter parts must be of sulfuric acid-stable material, e.g. Braun Biostat S (10l, glass body), Braun Biostat 50 D (50l, stainless steel body).

Starting from frozen cells, which have been conserved as described below, a 10-l fermenter can directly be inoculated without any preceding flask cultivation. The normal conditions in the case of fermenter cultivation are 59° C. and pH 2. After an optimum density of 0.4 (at 578 nm) has been reached, 1% by volume of yeast extract solution is added for the first time, after another 8 hours for the second time. The addition of yeast extract increases the pH in the medium and is compensated by the addition of corresponding amounts of 1 M sulfuric acid. After an optimum density (578 nm) of 0.6 to 0.7 has been reached, 5 l are taken from the 10-l fermenter culture as an inoculum for a 50-l fermenter. This fermenter is cultivated as usual, with 1% by volume of yeast extract being added after 20 hours and 28 hours, respectively. After the stationary phase has been reached, 1 liter is used as an inoculum for another 10-l fermenter.

*Thermoplasma acidophilum* is obligatorily aerobic, but high oxygen concentrations are not of advantage to growth. The oxygen regulation is set to 0.02 to 0.03 vvm (volume aeration per volume medium per minute) in the 10-l fermenter and to 0.04 vvm in the 50-l fermenter. During growth the oxygen content of the medium decreases constantly and rapidly until it can no longer be measured, but it need not be counter-regulated. The pH is constantly measured during cultivation and regulated at pH changes.

1.4 Cell Harvesting

The growth of *Thermoplasma acidophilum* reaches the stationary phase after about 40 hours ($OD_{578}$ of about 0.6). Harvesting should therefore be carried out at an $OD_{578}$ of 0.6, 0.7 at the most, after about 40 hours.

The cell culture from a 10-l fermenter is centrifuged in a Heraeus stock centrifuge at 3000×g for 15 minutes, the supernatant is discarded, the precipitate is resuspended in Freundt's solution. The suspension is centrifuged at maximum speed (4500 rpm, corresponding to about 3000×g) in a Christ centrifuge for 10 min, the process is repeated at least twice, with the Freundt's solution being replaced by sulfuric-acid Aqua bidist., pH 2, until the pellet is white. Finally, the white wet cell mass is suspended in Aqua bidist., frozen in methanol/dry ice and freeze-dried until constancy of weight.

The cell culture of the 50-l fermenter is concentrated to a volume of 2 l by means of a Pelikon tangential-flow filter system for harvesting purposes. This concentrate is washed with sulfuric-acid distilled water, pH 2, until the filtrate is clear and uncolored. The concentrated cell suspension is now centrifuged (see above), the pellet is resuspended in Aqua bidist., recentrifuged, resuspended, frozen and freeze-dried until constancy of weight.

1.5 Optical Control of the Purity of the *Thermoplasma-Acidophilum* Culture.

In the optical microscope, *Thermoplasma acidophilum* after the above cultivation appears to be between 1 and 3 $\mu$m in diameter at a cell density of $10^7$ cells/ml, mostly in isodiametric form; a few cells are pleiomorphic. Following laser light scattering in the Malvern Particle Sizer, the maximum of the size distribution is at 2.3 $\mu$m. Freeze-fracture electron micrographs show mostly round cells; pleiomorphic cells have longitudinal axes ranging between 1.1 and 2.7 $\mu$m and transverse axes of about 0.6 $\mu$m. The cells exhibit a typical fracture behavior which clearly distinghishes the cells from most other cells: their plane of fracture is perpendicular (transverse) to the plane of the membrane; it extends along the carbon hydrogen chains and not along the inner interface of the bilayer (tangential).

Under the given growth conditions (59° C., pH 2), only a few organisms can grow into the culture; e.g. *Bacillus acidocaldarius*. A cultivation at pH 1.5 prevents such a growth, but is accompanied with a loss in yield with respect to the desired lipid component. Hence, the cultivation optimum is at pH 2 under conditions that are as sterile ("germ-reduced") as possible.

1.6 Conservation

*Thermoplasma acidophilum* is conserved at $-80°$ C. or in liquid $N_2$. For conservation purposes an active culture (8–10 l) is set to a pH of 5.0–5.5 by adding calcium carbonate. After sedimentation of calcium sulfate and excess calcium carbonate (left to stand for at least 30 min), the supernatant is removed and centrifuged under sterile conditions at 3000×g for 15 min. The supernatant is discarded, and the *Thermoplasma acidophilum* cells of the pellets are resuspended in freshly prepared 10 mM sodium citrate buffer, pH 5.5. The suspension is portioned on ice in cryocups to 0.5 to 3.0 ml, the cryocups are frozen in liquid nitrogen for one hour and then kept therein or at $-80°$ C.

For cultivation purposes the cryocups with the cells are thawed in a water bath at 37° C.

It is essentially important to accomplish the conservation steps under sterile conditions because a pH of 1–2, which during cultivation prevents most microorganisms from growing in, is not observed.

EXAMPLE 2

Extraction and Purification of the Tetraether Lipids from *Thermoplasma Acidophilum*

2.1 Extraction of Total Lipid

The extraction of total lipid is performed with freeze-dried material. To this end 8 to 10 g of freeze-dried cell mass are continuously extracted with 300 ml of a petroleum ether (fraction 60 to 80° C.)/2-propanol mixture (77:23 v/v) in a Soxhlet device (recurring closed system) for 40 hours under reflux conditions. The described extraction is almost of a quantitative nature and leads to about 1 g of pure total lipid fraction. pb 750 mg of the total lipid fraction from *Thermoplasma acidophilum* are boiled in 800 ml of a 1 M HCl solution in methanol for 10 hours under reflux cooling conditions. After evaporation of the solvent the residue is dissolved in 100 ml $CHCl_3$ and washed with $H_2O$ (5×100 ml). The $CHCl_3$ fraction is evaporated and the residue is chromatographically separated through silica gel (silica gel, Merk; eluent $CHCl_3$). The fractions are collected and analyzed on TLC plates (mobile solvent: $CHCl_3$/methanol 9:1), already isolated tetraether serving as a standard (Freisleben et al., 1993, Appl. Microbiol. Biotechnol., 40, 745–52). After evaporation of the eluent the yield is about 390 mg tetraether lipids.

EXAMPLE 3

Preparation of Tetraether Lipid Derivatives A, B and C 3.1 Preparation of Dicarboxylic Acid Compounds 80 mg tetraether lipids are dissolved under stirring in a solution of 1 mg 4-methoxy-TEMPO radical in 2 ml $CH_2Cl_2$ at 4° C. (J. Org. Chem., 1985, 50, p. 1332). 5 ml of sodium hypochloride (0.35 M, pH 8.6) are added to the solution and the mixture is vigorously stirred at 4° C. for 5 min. After 30 ml $CHCl_3$ have been added, the organic phase is washed with 30 ml 0.25 M HCl five times. The organic phase is evaporated and the residue is chromatographically separated on silica gel (eluent: $CHCl_3$methanol/acetic acid 100:5:0.1). The fractions are collected and analyzed on a TLC plate (mobile solvent: $CHCl_3$/methanol/acetic acid 100:5:0.1). After evaporation of the eluent about 47 mg dicarboxylic acid compound are obtained from the corresponding fractions (about 50% yield).

3.2 Preparation of Dicarboxylic Acid Chloride 45 mg of the dicarboxylic acid compound are dissolved in a solution of thionyl chloride (100 $\mu$l) in 5 ml dry $CH_2Cl_2$ and refluxed. After about 6 hours the solvent is evaporated. The resulting dicarboxylic acid chloride can be used without any further purification steps.

3.3 Preparation of TEL Derivatives 3.2.1 Tetraether Lipid Derivative B

50 $\mu$l 4-dimethylaminopropylamine are added to a solution of about 45 mg dicarboxylic acid chloride in 5 ml dry $CH_2Cl_2$. After 5 min the mixture is washed with 30 ml water five times, the solvent is evaporated and the re sidue is chromatographically separated on silica gel (eluent: $CHCl_3$/methanol/acetic acid 80:20:0.5). The fractions are collected and analyzed on TLC plates with the same mobile solvent as indicated above. The solvent is evaporated from the fractions in which the tetraether lipid derivative A is determined. The process yields about 35 mg derivative B.

3.2.2 Tetraether Lipid Derivative A

Derivative A is obtained through a similar process in which, instead of 100 $\mu$l 3-dimethylaminopropylamine, 100 $\mu$l diaminopropane are used.

3.2.3 Tetraether Lipid Derivative C

Derivative C is obtained by dissolving derivative B in a solution of 10 $\mu$l dimethyl sulfate in $CH_2Cl_2$(5 ml). After 20 h the solvent is evaporated, the residue is dissolved in 10 ml $CHCl_3$ a nd respectively washed in 20 ml 0.1 M HCl three times. After evaporation of the organic solution about 10 mg derivative C are obtained (yield about 95%).

3.4 Preparation of a Fluorescence-Labeled Tetraether Lipid Derivative

For the clarification of the question as to whether the positively charged tetraether lipid derivatives according to the invention can penetrate into cells, a novel fluorescent tetraether lipid derivative has been synthetized.

Fluorescence-labeled tetraether lipid derivative is obtained by adding 2 mg rhodamine isothiocyanate and 5 $\mu$l triethylamine to a solution of 2 mg derivative A in 2 ml dry $CH_2Cl_2$. After 15 h the solution is washed with 30 ml water five times, the solvent is evaporated, and the residue is chromatographically separated on silica gel (eluent: $CHCl_3$/methanol/acetic acid, 80:20:0.5). The fractions are collected and samples thereof are analyzed on TLC plates. The fractions which contain the fluorescent lipid are pooled, and the solvent is evaporated. The process yields about 2 mg tetraether lipid rhodamine.

EXAMPLE 4

Preparation of Lipofection Agents

4.1. Empty Lipofection Agent

Tetraether lipid derivatives A, B or C are used for the preparation of lipofection agents. The tetraether lipid derivative is respectively dissolved (2 mg/ml) in chloroform/methanol (1/1, v/v) for the formation of lipofection agents. A lipid film is obtained by evaporating the solvent. The lipid film is hydrated in buffer A (150 mM NaCl, 50 mM Hepes, pH 7.4) at room temperature for 48 h (final concentration 0.5–2 mg lipid/500 µl, buffer A,), subsequently sonicated in an ultrasonic bath (Branson 1210) for 15 min and then sonicated with an ultrasonic tip (Branson B15, "cycle mode", position 40) at room temperature for 10 min. The lipid solution in buffer A appears to be turbid without any aggregates or recognizable precipitates.

4.2 DNA/Lipofection-Agent Complexes

4.2.1 Processes

For the preparation of DNA/lipofection-agent complexes, 3–5 µl of lipids suspended in buffer A (1 mg/ml) are dissolved in 100 µl serum-free medium. 1–2 µg DNA (1 mg/ml) are diluted in 100 µl serum-free medium. The two solutions are cautiously mixed and incubated at room temperature for 15 min to form DNA-lipid complexes. Typically, no aggregates are observed during complex formation. Prior to each transfection 800 µl serum-free medium are added, resulting in a final volume of 1 ml.

4.2.2 Detection of the Formation of DNA/Lipofection-Agent Complexes

Figure 2:
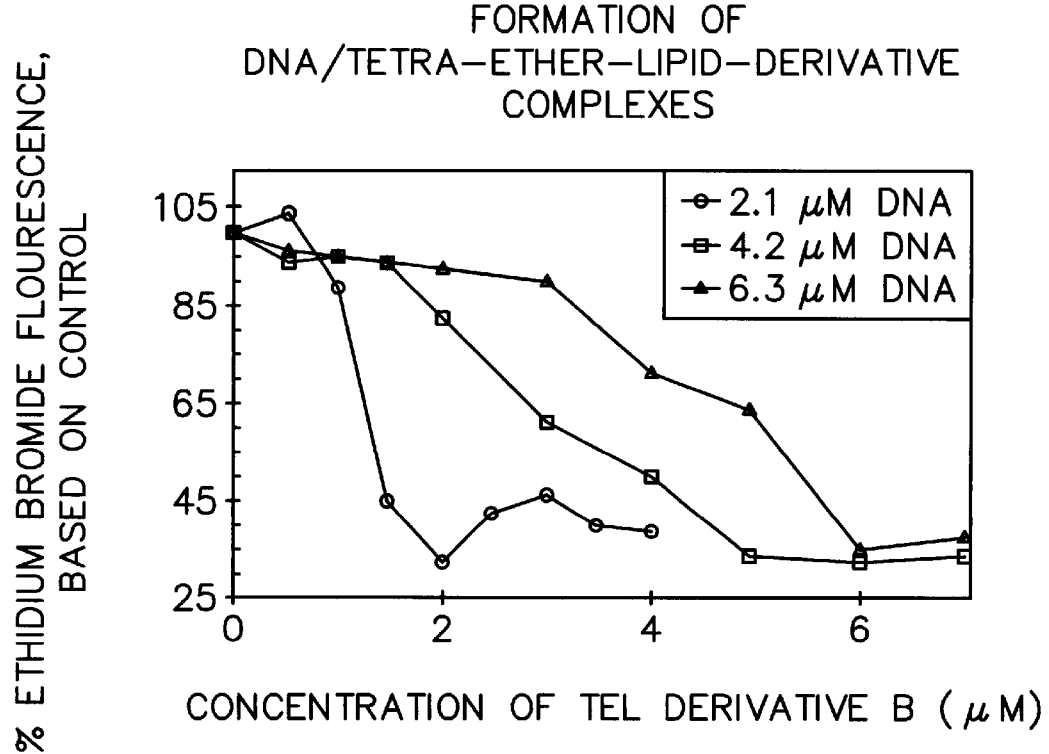
FIG. 2 shows the ethidium bromide fluoresence of DNA/tetraether-lipid-derivative complexes at different DNA-to-lipid ratios. The test underlying the figure is described in Example 4.2.2.

The formation of DNA/lipofection-agent complexes was analyzed fluorometrically. It is known that the formation of complexes from DNA and cationic lipids prevents ethidium bromide from binding to DNA (Gershon et al., Biochemistry 32, 7143–7151, 1993). Since the fluorescence of ethidium bromide-DNA complexes is proportional to the amount of free DNA in solution, this process can be used for quantifying DNA-lipid complexes. To this end DNA-lipid complexes of tetraether lipid derivative B and pSV-lacZ were prepared at different tetraether lipid derivate-to-DNA ratios in 1 ml 150 mM NaCl, 50 mM Hepes, pH 7.4. Subsequently, ethidium bromide was added up to a final concentration of $10^{-7}$ M. The fluorescence of ethidium bromide-DNA complexes was monitored by excitation at 518 nm and measurement of the emission at 605 nm. The results are shown in FIG. 2 and point out that DNA/tetraether-lipid-derivative complexes are formed at a molar ratio of 1:1.

Figure 3:
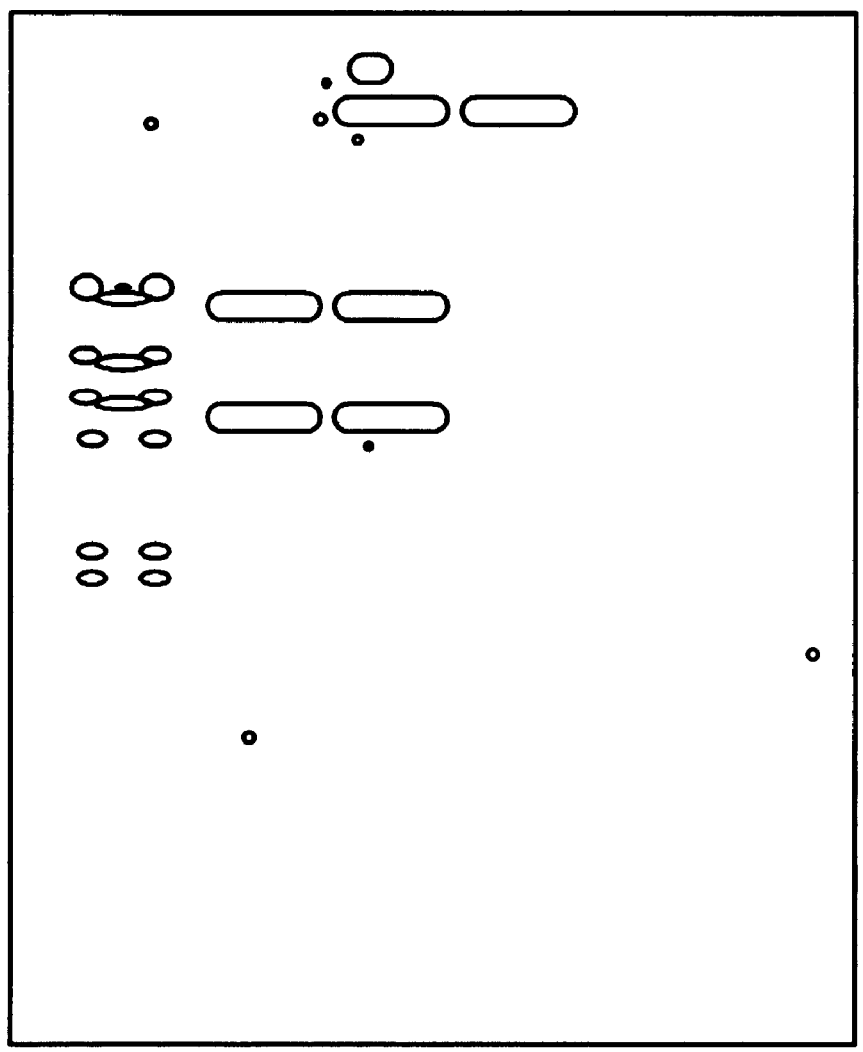
FIG. 3 shows an ethidium bromide-stained agarose gel (1%) on which DNA/tetraether lipid derivative complexes have been subjected to electrophoresis at different molar ratios of DNA to tetraether lipid. The DNA applied is pSV-lacZ; the TEL derivative used was compound B. Identical results have been obtained with compounds A and C. The lanes show in detail.

Moreover, formation of the complexes was shown using 1% agarose gels. In this independent test the formation of DNA/tetraether-lipid-derivative complexes is made visible through the disappearance of free DNA (FIG. 3, lane 4).

The results which have been obtained with two independently tests point out that the formation of tetraether-lipid-derivative/DNA complexes occurs at a molar ratio of 1:1.

EXAMPLE 5

Transfection with Tetraether Lipid Derivative-Containing Lipofection Agents

5.1 Transfection with PSV-lacZ

Transfections are carried out with a pSV-lacZ plasmid (Promega) as a reporter gene construct. $1 \times 10^5$ BHK (Baby Hamster Kidney) cells are plated on plates having 6 wells. After incubation in a $CO_2$-gassed atmosphere at 37° C. for 24 h the cells reach a density of 25–50% and can be used for transfection. Directly prior to transfection the cells are washed with 2 ml serum-free medium. 1 ml of the solution containing the DNA-lipid complex (see Example 4.2) is added. After 5 h the DNA-containing medium is replaced by normal growth medium containing 10% serum. Shorter incubation times (24 h) also lead to successful transfections.

19 h after transfection the cells are washed in PBS once, fixed with ice-cold methanol (−20°), washed with PBS three times and incubated in a solution of 4 mM Ferrycyanid (Sigma), 1 mM $MgCl_2$, 0.1% X-gal (Roth) in PBS, pH 7.4, for 16 h to detect the expression of β-galactosidase.

The transformation efficiency of the tetraether lipid derivatives A, B and C was compared with the commercially available transfection agents Lipofectin ® and Lipofectamin® (Gibco/BRL). The transfecton efficiency was indicated as a percentage of blue cells, based on the total cell number. The comparison revealed that the transformation efficiency for all of the inventive compounds was in the same order as for the commercial agents.

Furthermore, the optimum ratio of DNA to lipid was determined using the plasmid pSV-lacZ. The best transfection results were obtained at a molar ratio of 1:1 (DNA to lipid) (FIG. 4). The maximum β-galactosidase expression was observed 19 h after the beginning of the joint incubation of the cells with the DNA-lipid complex. As shown in FIG. 5, the transfection efficiency was 12% under these conditions, based on the total number of the cells used.

5.2 Transfection with Fluorescent Tetraether Lipid Derivatives

A fluorescence-labeled lipofection agent suspension is prepared by sonicating 1 mg of a mixture of tetraether lipid derivative A, B or C and tetraether lipid rhodamine (see Example 3.3) (100:1 molar ratio) in 1 ml of a buffer consisting of 150 mM NaCl, 50 mM Hepes, pH 7.4. The lipid concentrations of rhodamine-labeled liposomes or DNA-lipid complexes range from 10 to 100 µg/ml. The cells are incubated with the rhodamine-labeled lipofection agent at 38° C. for 70 min, washed with PBS three times and then analyzed in a "reverse fluorescent microscope".

The analysis revealed a diffuse fluorescence which could be observed in the cytoplasm of the cells (FIG. 1). The conclusion can be drawn from this result that the tetraether lipid derivatives according to the invention transverse the cell membrane.

6. Transfection Efficiency of Mixed Lipofection Agents

As shown in the literature (Felgner et al., Proc. Natl. Acad. Sci. 84, 7413–7417, 1987), increased transfection rates can be achieved by mixing Lipofectin® with DOPE (Sigma) (1:1, w/w). Therefore, the influence of the addition of various lipids to the tetraether lipid derivatives according to the invention was examined as to the efficiency of cell transfection.

The following was added: MPL (total phospholipid fraction from *Thermoplasma acidophilum*), PC (phosphatidylcholine) and DOPE (dioleylphosphatidylethanolamine). It could be observed that the mixture of the inventive tetraether lipid derivatives A, B or C with MPL in a ratio of 1:1 (w/w) does not impair the transfection efficiency, whereas the mixture of the inventive tetraether lipid derivatives at a mixing ratio of 1:2 (molar ratio of tetraether lipid derivative to MPL) considerably impairs the transfection efficiency. A mixture of tetraether lipid derivatives according to the invention with DOPE (molar ratio of 1:1) increases the transfection efficiency whereas a mixture of tetraether lipid derivative with PC (molar rato of 1:1) decreases the efficiency.

It follows from said tests that DOPE is a promising addition to tetraether lipid derivative A. The results are graphically illustrated in FIG. 6.

What is claimed is:

1. A tetraether lipid derivative represented by the general formula [I]:

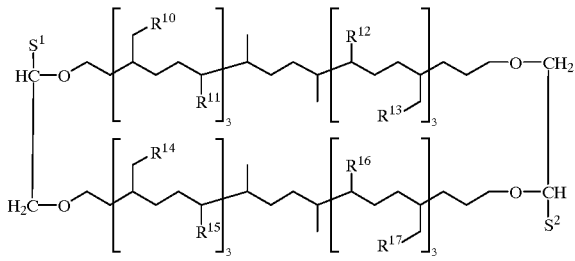

wherein each of $S^1$ and $S^2$ independently has the following meaning:

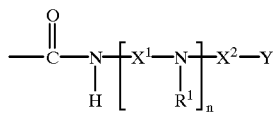

Y is $-NR^2R^3$ or $-N^+R^4R^5R^6$;

$X^1$ and $X^2$ are independently selected from the group consisting of alkylenes and alkenylenes having 2 to 20 carbon atoms;

$R^1$ to $R^2$ are independently selected from the group consisting of hydrogen and alkyl, alkenyl, aralkyl, and aryl groups having 1 to 12 carbon atoms, wherein one of $R^2$ to $R^6$ can, optionally, further comprise an antibody against cell surface molecules or a ligand for cell surface receptors;

each $R^{10}$ and $R^{11}$ pair are either each —H or, together, a covalent bond;

each $R^{12}$ and $R^{13}$ pair are either each —H or, together, a covalent bond;

each $R^{14}$ and $R^{15}$ pair are either each —H or, together, a covalent bond;

each $R^{16}$ and $R^{17}$ pair are either each —H or, together, a covalent bond; and n is an integer from 0 to 10.

2. The tetraether lipid derivative of claim 1, wherein $S^1$ and $S^2$ are the same.

3. The tetraether lipid derivative of claim 1, wherein $X^1$ is selected from the group consisting of alkylenes and alkenylenes having 2 to 10 carbon atoms.

4. The tetraether lipid of claim 1, wherein $X^2$ is selected from the group consisting of alkylenes and alkenylenes having 2 to 10 carbon atoms.

5. The tetraether lipid derivative of claim 1, wherein n is 0 to 3.

6. The tetraether lipid of claim 1, wherein Y is $-NR^2R^3$ and wherein each of $R^2$ and $R^3$ is independently selected from the group consisting of —H, —$CH_3$, —$C_2H_5$, and —$C_3H_7$.

7. The tetraether lipid derivative of claim 1, wherein Y is $-N^+R^4R^5R^6$ and wherein each of $R^4$, $R^5$, and $R^6$ is independently selected from the group consisting of —H, —$CH_3$, —$C_2H_5$, and —$C_3H_7$.

8. The tetraether lipid derivative of claim 1 wherein each of $S^1$ and $S^2$ has the following meaning:

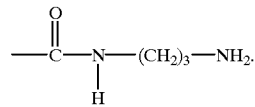

9. The tetraether lipid derivative of claim 1 wherein each of $S^1$ and $S^2$ has the following meaning:

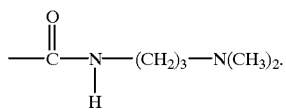

10. The tetraether lipid derivative of claim 1 wherein each of $S^1$ and $S^2$ has the following meaning:

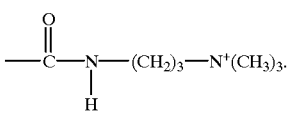

11. A liposome comprising the tetraether lipid derivative of claim 1.

12. The liposome of claim 11, further comprising a lipid selected from the group consisting of a bilayer-forming cationic lipid and a neutral lipid.

13. The liposome of claim 12, wherein said lipid is a bilayer-forming cationic lipid selected from the group consisting of DOTMA, DOTAP and DOSPER.

14. The liposome of claim 12, wherein said lipid is a neutral lipid selected from the group consisting of DOPE and cholesterol.

15. The liposome of claim 11, wherein the liposome comprises a lipid which is not a tetraether lipid derivative, and further wherein the weight ratio of said tetraether lipid derivative to said non-tetraether lipid is 5:1 to 1:5.

16. The liposome of claim 15, wherein the weight ratio of the tetraether lipid derivative to the non-tetraether lipid is 1:2 to 1:0.5.

17. The liposome of claim 15, wherein the weight ratio of the tetraether lipid derivative to the non-tetraether lipid is 1:1.

18. The liposome of claim 11, further comprising a nucleic acid molecule.

19. A composition comprising the liposome of claim 11 and a physiologically compatible diluent.

20. An in-vitro transfection kit comprising the liposome of claim 11 and a suitable buffer.

21. A method of transfecting a cell in vitro, said method comprising contacting a cell with a complex of plasmid DNA and the liposome of claim 11, whereby the plasmid DNA enters the cell.

22. A lipid agglomerate comprising a layer which comprises the tetraether lipid derivative of claim 1.

23. The lipid agglomerate of claim 22, further comprising a lipid selected from the group consisting of bilayer-forming cationic lipids and neutral lipids.

24. Tle lipid agglomerate of claim 23, wherein said lipid is a bilayer-forming cationic lipid selected from the group consisting of DOTMA, DOTAP, and DOSPER.

25. The lipid agglomerate of claim 23, wherein said lipid is a neutral lipid selected from the group consisting of DOPE and cholesterol.

26. The lipid agglomerate of claim 22, wherein the agglomerate comprises a lipid which is not a tetraether lipid derivative, and further wherein the weight ratio of said tetraether lipid derivative to said non-tetraether lipid is 5:1 to 1:5.

27. The lipid agglomerate of claim 22, wherein the weight ratio of the tetraether lipid derivative to the non-tetraether lipid is 1:2 to 1:05.

28. The lipid agglomerate of claim 22, further comprising a nucleic acid molecule.

29. A composition comprising the lipid agglomerate of claim 22 and a physiologically compatible diluent.

30. An in vitro transfection kit comprising the lipid agglomerate of claim 22 and a suitable buffer.

31. A method of transfecting a cell in vitro, said method comprising contacting a cell with a complex of plasmid DNA and the lipid agglomerate of claim 22, whereby the plasmid DNA enters the cell.

32. The lipid agglomerate of claim 22, wherein the weight ratio of the tetraether lipid derivative to the non-tetraether lipid is 1:1.

33. The tetraether lipid derivative of claim 1, wherein $X^1$ is selected from the group consisting of alkylenes and alkenylenes having 3 to 6 carbon atoms.

34. The tetraether lipid derivative of claim 1, wherein $X^2$ is selected from the group consisting of alkylenes and alkenylenes having 3 to 6 carbon atoms.

35. The tetraether lipid derivative of claim 1, wherein n is 0.

* * * * *

UNITED STATES PATENT AND TRADEMARK OFFICE
CERTIFICATE OF CORRECTION

PATENT NO. : 6,316,260 B1
DATED : November 13, 2001
INVENTOR(S) : H.-J. Freisleben, Emmanouil Antonopoulos, Maxim Balakirev, Larissa Balakirev, Klaus Hartmann and Felix Gropp It is certified that error appears in the above-identified patent and that said Letters Patent is hereby corrected as shown below:

<u>Title page,</u>
Item [30], insert
-- Foreign Application Priority Data
August 22, 1997 (DE)..........................19736592.2 --

<u>Column 15,</u>
Beginning at line 1, claim 1 is amended to read --
1. A tetraether lipid derivative represented by the general formula:

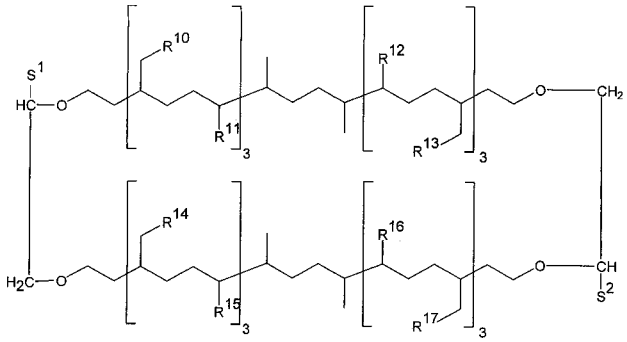

wherein each of $S^1$ and $S^2$ independently has the following meaning:

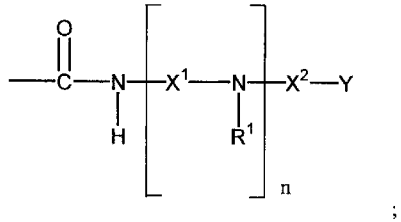

;

| | |
|---|---|
| Y | is $-NR^2R^3$ or $N^+R^4R^5R^6$; |
| $X^1$ and $X^2$ | are independently selected from the group consisting of alkylenes and alkenylenes having 2 to 20 carbon atoms; |
| $R^1$ and $R^6$ | are independently selected from the group consisting of hydrogen and alkyl, alkenyl, aralkyl, and aryl groups having 1 to 12 carbon atoms, wherein one of $R^2$ to $R^6$ can, optionally, further comprise |

UNITED STATES PATENT AND TRADEMARK OFFICE
CERTIFICATE OF CORRECTION

PATENT NO. : 6,316,260 B1
DATED : November 13, 2001
INVENTOR(S) : H.-J. Freisleben, Emmanouil Antonopoulos, Maxim Balakirev, Larissa Balakirev, Klaus Hartmann and Felix Gropp It is certified that error appears in the above-identified patent and that said Letters Patent is hereby corrected as shown below:

an antibody against cell surface molecules or a ligand for cell surface receptors;
each $R^{10}$ and $R^{11}$ pair are either each -H or, together, a covalent bond;
each $R^{12}$ and $R^{13}$ pair are either each -H or, together, a covalent bond;
each $R^{14}$ and $R^{15}$ pair are either each -H or, together, a covalent bond;
each $R^{16}$ and $R^{17}$ pair are either each -H or, together, a covalent bond; and
n is an integer from 0 to 10. --

Signed and Sealed this

Second Day of July, 2002

*Attest:*

*Attesting Officer*

JAMES E. ROGAN
*Director of the United States Patent and Trademark Office*